(12) United States Patent  
Sorensen et al.

(10) Patent No.: US 8,117,512 B2  
(45) Date of Patent: Feb. 14, 2012

(54) FAILURE DETECTION AND MITIGATION IN LOGIC CIRCUITS

(75) Inventors: Steen Ditlev Sorensen, Scottsdale, AZ (US); Sten Sogaard, Anthem, AZ (US)

(73) Assignee: Westinghouse Electric Company LLC, Cranberry Township, PA (US)

( * ) Notice: Subject to any disclaimer, the term of this patent is extended or adjusted under 35 U.S.C. 154(b) by 166 days.

(21) Appl. No.: 12/401,559

(22) Filed: Mar. 10, 2009

(65) Prior Publication Data

US 2011/0209021 A1 Aug. 25, 2011

Related U.S. Application Data

(63) Continuation-in-part of application No. 12/026,703, filed on Feb. 6, 2008, now Pat. No. 7,870,299.

(51) Int. Cl.
*G01R 31/28* (2006.01)
*H03M 13/00* (2006.01)
*G06F 11/00* (2006.01)

(52) U.S. Cl. ........ 714/733; 714/758; 714/760; 714/799; 714/30; 714/48

(58) Field of Classification Search .................. 714/733, 714/758, 760, 799, 30, 48
See application file for complete search history.

(56) References Cited

U.S. PATENT DOCUMENTS

| | | | | |
|---|---|---|---|---|
| 4,517,639 A * | 5/1985 | Ferrell et al. | ............... | 700/81 |
| 4,903,270 A * | 2/1990 | Johnson et al. | ............... | 714/820 |
| 4,980,857 A * | 12/1990 | Walter et al. | ............... | 714/45 |
| 5,134,619 A * | 7/1992 | Henson et al. | ............... | 714/770 |
| 5,144,230 A | 9/1992 | Katoozi et al. | | |
| 5,581,713 A * | 12/1996 | Myers et al. | ............... | 710/119 |
| 5,586,156 A * | 12/1996 | Gaubatz | ............... | 376/216 |
| 5,787,095 A * | 7/1998 | Myers et al. | ............... | 714/820 |
| 6,233,702 B1 | 5/2001 | Horst et al. | | |
| 6,298,289 B1 * | 10/2001 | Lloyd et al. | ............... | 701/13 |
| 6,985,975 B1 * | 1/2006 | Chamdani et al. | ............... | 710/55 |
| 7,075,427 B1 * | 7/2006 | Pace et al. | ............... | 340/539.22 |
| 7,134,104 B2 | 11/2006 | Goodnow et al. | | |
| 7,237,144 B2 | 6/2007 | Safford et al. | | |
| 7,284,152 B1 * | 10/2007 | Barthel et al. | ............... | 714/12 |
| 7,290,169 B2 | 10/2007 | Safford et al. | | |
| 7,406,632 B2 * | 7/2008 | Sealey et al. | ............... | 714/48 |
| 7,472,051 B2 * | 12/2008 | Mariani et al. | ............... | 703/13 |
| 2007/0022348 A1 | 1/2007 | Racunas et al. | | |

* cited by examiner

*Primary Examiner* — John J Tabone, Jr.

(57) ABSTRACT

The present invention is directed to methods of monitoring logic circuits for failures. In particular, the methods are directed toward establishing parallel logic cores where failures are detected by comparing the parallel paths for equivalence at key locations by a redundancy checker. Any mismatch will result in a predetermined failsafe operational mode. In addition, important techniques are applied to periodically exercise individual parallel paths to ensure that logic cores are verified in a way that does not disturb any process being monitored or controlled. This feature is important in some industries, such as the nuclear power industry, where safety critical operations require a high state of reliability on logic circuit blocks which may be infrequently utilized.

30 Claims, 4 Drawing Sheets

FAILURE DETECTION AND MITIGATION IN LOGIC CIRCUITS

CROSS REFERENCE TO RELATED APPLICATIONS

This application is a continuation-in-part of U.S. patent application Ser. No. 12/026,703, filed on Feb. 6, 2008 now U.S. Pat. No. 7,870,299. The entire prior application is hereby incorporated herein by reference.

STATEMENT REGARDING FEDERALLY SPONSORED RESEARCH OR DEVELOPMENT

Not applicable.

REFERENCE TO SEQUENCE LISTING, A TABLE, OR COMPUTER PROGRAM LISTING

Not applicable.

BACKGROUND OF THE INVENTION (1) Field of the Invention

The present invention generally pertains to a method for designing high integrity logic circuits. It is particularly directed toward safety-related control systems, including nuclear plant reactor protection systems, where integrity and reliability are of the highest importance. The present invention is especially directed toward implementing the methods in a logic device such as PAL, CPLD, FPGA, ASIC, or Gate Array, or in a combination of multiple logic devices. Such logic devices are commonly installed on printed circuit boards.

(2) Description of Related Art

Others have attempted to improve the reliability of mission critical logic components in a computerized system. For example, U.S. Pat. No. 7,290,169 describes a core-level processor lock stepping system where two microprocessors are operated in parallel, and they each provide an external output signal which is compared. The microprocessors are meant to operate in lockstep, that is, to operate in a tightly coordinated manner so that their outputs will match in a reliable manner. In actual practice, this method has a number of problems for safety critical systems. It is difficult to keep the microprocessors completely in lockstep. There can be hidden failures in the system which are not uncovered until a system is actually used.

U.S. Pat. No. 7,237,144 provides similar operational thinking and difficulties but provides off chip lockstep checking to combat "soft errors." It has the same difficulties as just described.

U.S. Pat. No. 6,233,702 describes a complicated multiple processor system providing fault tolerant data processing by employing hardware (e.g. fail functional, employing redundancy) and using software techniques (fail fast e.g. employing software recovery with high data integrity hardware). The error checking specifically avoids the utilization of redundancy to compare key data points between parallel processors, and instead only compares points that operate at slower rates such as at I/O points or in the main memory. This design is overly complicated and has a problem with unannounced errors which will be discussed shortly. It is a software based system with problems that will also be discussed shortly.

U.S. Pat. No. 7,134,104 describes a method of improving fault tolerance in an FPGA by creating at least three parallel copies of logical functions, and then using a voting scheme to determine if any particular copy is faulty. While this method generally improves fault tolerance, it is not a satisfactory scheme for a safety critical environment where it cannot be certain that the majority vote is always the non-faulty result.

U.S. Pat. No. 5,144,230 describes a self test circuit by a method called cycle stealing. The output signal from a 'circuit under test' is tested by selectively applying a test input signal when the output signal is not required to perform it normal function. Though this is one possible method of checking a processor, the testing does not provide any protection against failures affecting dependent systems. When parallel redundancy is used, a voter scheme is used to determine the non-faulty result. These methods are unacceptable for a safety critical environment where a highly reliable system is desired.

US application 2007/0022348 describes parallel lock step cores which are similar to U.S. Pat. No. 7,290,169 already described except that intermediary values from the cores are also compared along with outputs. However, this system has all of the problems in maintaining two cores in lockstep. For example, when there is an error, caches have to be loaded into the system memory to ensure the lockstep is maintained going forward. The caches have to be maintained and verified on an ongoing basis when there are system or programming changes. The system is also software based.

There is a need in the art to provide a highly reliable system that is not a software based system. For example, in a safety critical system, such as a nuclear plant protection system, it is undesirable to be dependent upon executable software due to the nature of potential errors. Software has inherent operational problems that are difficult to resolve. Even relatively simple systems require a significant amount of program code. In particular, a software-microprocessor system is subject to common mode failure where parallel redundant systems may fail simultaneously due to a fault condition.

In spite of redundancy that may be included within software-microprocessor systems, a fault may occasionally affect enough redundant functions that it is not possible to correctly pick a non-faulty result, and the system will experience a common-mode failure. The common-mode failure may result from a single fault or several faults. It is known that microprocessor based systems are vulnerable to common-mode failures where redundant copies of software fail under the same fault. The common-mode fault, in particular, makes software-microprocessor systems undesirable in a plant protection system.

For the purposes of the present invention, the following definitions apply. A failure is the termination of the ability to perform a required function. See also mission failure. Failures may be unannounced and not detected until the next test which is called an unannounced failure. They may be announced and detected by any number of methods at the instant of occurrence which is called an announced failure. A mission is the singular objective, task, or purpose of an item or system. A mission failure is the inability to complete a stated mission within stated limits. Critical functions are the functions needed in a logic circuit in order for it to perform its mission.

In a safety related control system, a high integrity system will have two critical features:
1) It will perform its mission when called upon. The mission will typically be to actuate field devices when a predefined set of input conditions are present. To have a high assurance of performing its mission when called upon, no unannounced failures must exist in system. Unannounced failures can cause the system to malfunction at the moment its mission is called upon. This means all failures must be detected and announced.

2) Unintended actuations of the control system due to logic circuit failures must be avoided. These actuations cause the field devices to perform their safety functions which are often costly. To do this all failures must be isolated contained before they reach the field device.

A common method for increasing reliability and availability in logic circuits used in critical applications is to use triple or more redundancy (TMR). This is commonly done in nuclear, space and military applications. Having TMR logic circuits, with a majority voting scheme allows for fault tolerance. If a majority of the redundant logic circuits are without failures, the system will perform its function. Unfortunately, if the majority is in error compared to the minority, the system will be utilizing an error in its function.

If failures are allowed to accumulate in a TMR system it could have catastrophic effects. In particular, if it is applied to a safety critical application, the system could fail in its function to shut a system down or take appropriate corrective action to eliminate a problem before it becomes critical.

Failures in TMR logic circuits can be detected by comparing the output between the redundant logic circuits. However it cannot detect unannounced failures, i.e., failures in logic circuits which do not result in an output change. Unannounced failures in the system are not found until the particular logic function is exercised. That is, until the particular logic pathways are utilized.

Unannounced failures are particularly a problem in nuclear safety systems which are normally in a "waiting" position where no inputs or outputs are changing state. The Safety Systems may remain in this state for extended periods of time allowing unannounced failures to accumulate. Unannounced failures may sit undetected for weeks, months, or even years.

Adding TMR to a system inherently adds complexity which reduces overall reliability. Maintenance is increased by the additional logic and programming added. Adding additional redundant modules (4 or more) will improve protection against unannounced failures by decreasing their probability of building up and affecting the voting logic, but at the expense of a proportional decrease in reliability and increase the complexity.

BRIEF SUMMARY OF THE INVENTION

The present invention is directed to methods of creating high integrity logic circuits and monitoring them to verify their correct operation. In particular, the methods are directed toward establishing parallel logic circuit cores where failures are detected by comparing the parallel paths for equivalence at key locations by a redundancy checker. Any mismatch will result in a predetermined failsafe operational mode. In addition, methods are developed to periodically exercise individual parallel paths to ensure that the logic circuit paths are exercised in a way that will expose unannounced failures while not disturbing any process being monitored or controlled.

BRIEF DESCRIPTION OF THE SEVERAL VIEWS OF THE DRAWING(S)

DETAILED DESCRIPTION OF THE INVENTION

Figure 1:
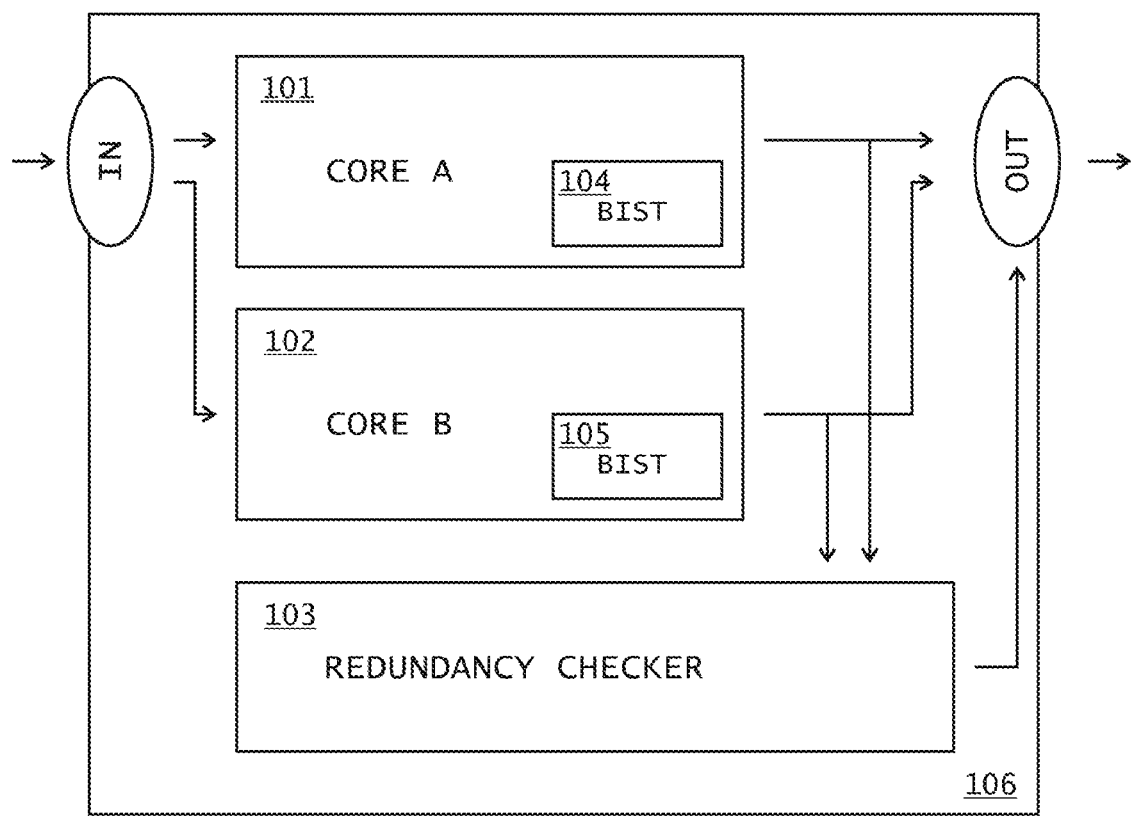
FIG. 1 shows a graphic illustration of the implementation of two parallel cores utilizing a redundancy checker.

A primary object of the present invention is to provide for a highly reliable logic circuit, with assurance that it can perform the intended mission when called upon.

Another object of the present invention is to provide for a method for designing fail-safe logic circuits that are implemented in a single logic device such as PAL, CPLD, ASIC, Gate Array, or FPGA. Alternately and equally, the logic circuits are implemented in a combination of multiple logic devices on a single printed circuit board (PCB). Alternately and equally, they are implemented in a combination of multiple printed circuit boards with one or more logic devices such as PAL, CPLD, FPGA, ASIC, or Gate Array.

The invention may be combined with redundancy and/or fault tolerance at an application level by having multiple parallel systems capable of performing the mission. One method is to have two or more parallel systems capable of performing the missions. If one of these systems fails and enters a failsafe state, the other system(s) remains capable of performing the mission. Another method to improve integrity is to have three or more parallel logic circuit cores where two are used to provide failsafe operation, and a third logic core offline in a testing mode. The cores are then periodically rotated so that at least two cores are always online and one is always being tested. Alternately, a testing schedule is established so that all cores are normally online, and periodically one core is taken offline for testing.

The parallel logic cores are exactly replicated, or they are similarly replicated to perform the same mission. In the latter case the cores are diversely replicated cores or parallel diverse cores.

The present invention is applicable to industrial process monitoring and control. The present invention is particularly directed toward safety critical control systems, including nuclear plant reactor protection systems, where reliability and integrity are of the highest importance.

Any logic circuit is susceptible to errors such as:

1. Single Event Effects (SEEs) caused by cosmic rays or high energy protons, Single event Upsets (SEUs) causing transient pulses in logic, bitflips in memory cells and registers, and Single Event Latchup (SEL).
2. Electrostatic discharge (ESD) and electrical overstress (EOS).
3. Flash cell decay/failure caused by device failure, device design failure, or excessive heating.
4. Manufacturing failures and/or aging related failures, such as oxide failures, metal layer failure, electron migration, bonding wire erosion, contamination effects from moisture, or chemicals used in the process etc.

In a safety critical system, such as a nuclear power plant, the above items are of increased concern and importance.

Common for all of the above failures is that they usually occur randomly in time and location, and typically only affect one or a few transistors. These errors can cause significant problems.

The present invention describes a method for designing logic circuits where failures are automatically detected and mitigates in a manner where other dependent systems are not adversely affected.

The present invention provides for a minimal addition of complexity and increases the overall reliability with a minimum of maintenance.

The present invention may be combined with fault tolerance schemes.

One embodiment of the present invention is a combination of the following three techniques:
1. Use of parallel redundant cores to ensure all failures are instantly detected and isolated by a redundancy checker.
2. Use of a built in self test engine to exercise critical functions within the core to protect against unannounced failures. Failures are unannounced if they are undetected prior to actual use.
3. Parallel redundant core interface to external communication is inherently protected by:
   a) Serial or parallel interfaces are protected by redundancy or Cyclic Redundancy Checks (CRC).
   b) 'Toggle test' on inputs. A toggle test is a method to ensure that input circuits and their connections are functional. This test typically includes disconnecting the input from the sourcing device and applying test input signals to the logic circuit. If the input mirrors the test input it can be determined that the input circuit is functional.
   c) Independent read back of outputs. This is an independent method of verifying the state of an output by including feedback to an input. An example would be by verifying that a relay is in fact actuated when requested by using a spare contact on the relay to drive an input. Various other analog and digital outputs may wired to an input in series or parallel for verification in this manner.

In a preferred embodiment of the present invention, a built-in self-test (BIST) structure is placed on a programmable logic device and its function is performed in a manner that does not affect the logic circuit output. An important feature of the BIST is to expose any unannounced failures in the parallel cores. The BIST has important functions as follows:
1. The BIST engine tests the parallel cores by applying pseudo random input stimuli.
2. The BIST engine tests the parallel cores by applying a planned or programmed input stimuli sequence.
3. It tests all state transitions and output combinations.
4. It verifies the parallel cores ability to perform its mission.
5. It does any single item or combination of the above.

Additionally, in one embodiment, the BIST tests the parallel cores by:
1. Monitoring critical internal states from the cores.
2. Monitoring critical outputs from the cores.
3. Testing two redundant cores against each other by comparison at selected places.
4. 'Accumulating' the internal state from each parallel core into a checksum.
5. 'Accumulating' the output response from each parallel core into a checksum.
6. It does any single item or combination of the above.

In an important embodiment, a test method whereby the BIST verifies the parallel cores is to:
1. Place a one of the parallel cores in a test mode so that it does not affect the status of any input or output,
2. Disable the redundancy checker for the core being tested,
3. Apply a set of predetermined inputs to at least one input or internal states to the core being tested as previously described.
4. Verify the response of the core to the inputs by monitoring internal state changes and core outputs against a checksum or against a predetermined pattern.
5. Restore the core and the disabled redundancy checker to normal operation.

Another embodiment test method whereby the BIST verifies the parallel cores is to:
1. Place the logic circuit into a test mode where the status of any output is not affected,
2. apply a set of identical predetermined inputs to all of the parallel cores as previously described,
3. verify the response of all of the parallel cores by the redundancy checker.

In a preferred embodiment, multiple barriers exist to ensure that the logic circuit cannot continue operation after a redundancy error occurs. In a plant protection environment, a failsafe signal is sent to all affected parallel cores to stop all operation. All proper functioning cores will obey this signal and stop operation. One of mismatched parallel cores, which causes this condition, may not be able to obey this signal for the same reason that causes the error. To resolve this:
1. Communication to other systems are constructed in a way where the parallel cores must match in order to succeed. This way the failed logic circuits cannot communicate erroneous data to unaffected/dependent systems. This is done by:
   a) AND or OR gate of communication data, to intentionally create an invalid CRC checksum.
   b) AND Gate ON communication data output enable. This prevents data from being transmitted.

The preferred embodiment of the present invention is to utilize FPGAs to implement the primary control functions. In other embodiments, alternatives to FPGAs are used which include ASICs (Application Specific Integrated Circuits), CPLD (Complex Programmable Logic Device), Gate Arrays, and PAL (Programmable Array Logic). These devices are generally called programmable logic devices, complex logic devices, or logic devices. All of these devices may be utilized through suitable programming to operate without the use of executable software. A system governed by these devices could be described as hardware based.

A logic device is programmed utilizing logic which is customizable based on the requirements of a given application, and contains any type of digital building block which typically comprise: AND gate, OR gate, XOR gate, Flip Flops (D, JK, SR), counters, timers, multiplexers, and Finite State Machines (FSMs). When programmed properly, the logic device will behave in a highly predictable, substantially deterministic manner.

In an important embodiment, the logic circuit is described at a register transfer level which includes hardware description languages such as Verilog or VHDL, and schematic captures. The entire logic circuit, or critical functions of the logic circuit, is replicated by redundant cores. The inputs to the cores are designed in a manner that ensures that the inputs are transferred error free into an internal core register.

The logic circuit will receive external inputs. The inputs to the logic circuit may include any of: serial interfaces protected with redundancy, discrete inputs, or digitized analog values. Critical inputs are ensured by redundancy testing, XOR toggle test, CRC and/or external loopback test. Any input testing is implemented in a manner that does not affect the input data. Typical input circuits include: bus communication circuits (serial and parallel), digital channels (serial and parallel), communication circuits (serial and parallel), digital circuits (serial and parallel), and digitized analog circuits.

The outputs from the parallel cores are designed in a manner to ensure that the outputs are functional. The assurance comes from redundancy testing, XOR toggle testing, CRC and/or external loopback test. An external loopback test is an independent verification of an output signal by routing the output signal back to an input. The output signal is then compared to an actual measured value. Typical output circuits include: bus communication circuits (serial and parallel), digital channels (serial and parallel), communication circuits (serial and parallel), digital circuits (serial and parallel), and digitized analog circuits.

I/O from the logic circuit typically comprise the following important features:
1. Serial or parallel interfaces protected with redundancy.
2. Serial or parallel interface from the redundant cores are AND'ed or OR'ed by the redundancy checker in the CRC to ensure all communication to other systems will stop when a failure occurs due to a CRC failure in communication.
3. Inputs from discrete inputs.
4. Discrete outputs which can drive relays, solid state relays, field components, or other system inputs.
5. Critical outputs are tested by such means as
    a) Ensured by redundancy,
    b) XOR toggle test,
    c) CRC, and
    d) external loopback test.
    The output test is implemented in a manner which does not cause undesired field actuations.

In a preferred embodiment, a BIST is implemented by:
1. Being designed to exercise critical functions, such as traversing all states in a finite state machine or only a particular set of states.
2. The critical function of the logic circuit is determined and tested for satisfactory operation. This may include all functions of the circuit.
3. Injecting test input signals in a manner where there can be no stuck-at faults in the logic circuit.
4. Being designed in such a manner that it does not affect the output. This may be done by:
    a) Freezing outputs during the test, or
    b) Performing the test in periods of time where outputs are not updated.
5. Verifying operation of the logic circuit by:
    a) Having the BIST engine verify functionality by monitoring internal states, i.e. key values or registers in a core which are also called critical states, and the core outputs. A form of data compaction may be used to simplify core output or internal state condition based on the BIST input stimulation.
    b) Having multiple BIST engines run synchronous routines between the redundant cores. In this case the BIST engines do not need to verify output. This will be done by the redundancy checker which can compare the two cores at key points, or compare the outputs of the two cores for a match.
6. Upon completion of a BIST, the logic circuit is restored to its proper state. That is, any parallel cores that were tested are restored to normal operation.

In a preferred embodiment, a redundancy checker logic circuit is used to determine if the logic circuit is faulty, and places the logic circuit in a failsafe state. The redundancy checker monitors key redundancy check points in the logic circuit structure, that is, signals from a particular circuit from each of the redundant logic cores are wired to a redundancy checker logic circuit. The redundancy checker then looks for discrepancies between the two cores by comparing the two signals from each of the redundant cores for an exact match. If the values do not match, a redundancy failure (i.e. error) is detected. Additionally, the redundancy checker is implemented by comparing critical signals (i.e. critical data) which preferably includes both critical internal states and outputs.

In a preferred embodiment, and because the system is hardware based, there should not be a mismatch between the parallel redundant cores. They receive the same input at the exact same time, and the cores will operate in perfect synchronicity.

By monitoring internal states and outputs form each redundant core, the redundancy checker will instantly detect a state change of a critical function, such as a unintended actuation signal being generated by a core because of a failure. Without the redundancy checker to mitigate this failure and force the logic circuit into a failsafe state, the failure would propagate to dependent systems and cause undesired plant transients.

In a preferred embodiment, critical functions of the logic circuit that are monitored by the redundancy checker include: logic decision, limit check, state machines, detection logic, and control logic.

In another important embodiment of the present invention, the parallel cores are not exactly replicated. That is, the parallel cores accomplish the same mission or function, but by a diversity in design. The cores are said to be parallel diverse cores. The diversity can be established by how the program is physically placed within an FPGA for example, by changing how the interconnect resources are used, or for minor programming differences between programmers who are given the same assignment. The diversity could be very large if different logic devices are used in the implementation, e.g. different FPGA vendors or using a microprocessor to perform portions of the logic.

Diversity is a very important operational safety feature to ensure that a programming error will not affect the overall safety of an operation. Two, three, or more cores can be programmed separately; by two or more programmers. To enhance diversity, different programmers are tasked to take different approaches, even with a fairly straightforward programming mission. Methods to ensure diversity or different implementation include diverse state encoding, "one hot" vs. "gray codes," utilizing hierarchical optimization or not, utilizing flattening or not, and how the program is laid out on the complex logic device.

In the case of utilizing the parallel diverse cores, the redundancy checker compares values from selected points within the cores, values from the output points, or both.

In one embodiment of the present invention, diversity can be extended to include the use of a microprocessor with executable software in parallel to a FPGA based system free of the use of executable software. For example, one parallel core could be implemented in a logic device and another parallel core in a software based processor device. A redundancy checker would then be used to look at the outputs from both cores to monitor for mismatches.

In the case of a software based parallel core, a built in self test would include features to ensure correct operation and the detection of unannounced failures by using a combination of watch dog, runtime assertions and self testing. In a preferred embodiment, a software based BIST would be designed to test the processor by using the techniques already described such as exercising critical functions, injecting test input signals, freezing outputs during the test, performing the test in periods of time where outputs are not updated, verifying operation of the processor, and verifying functionality by monitoring key values or registers. Upon completion of a BIST, the processor is restored to its proper state.

FIG. 1 shows a graphic illustration of the implementation of two parallel cores utilizing a redundancy checker. A first CORE A 101 and a second CORE B 102 are parallel and redundant representations of a logic circuit. A REDUNDANCY CHECKER circuit 103, already described, is used to verify the integrity operation of the cores. A BIST 104, 105 is shown as part of each of the core structures, but alternately and equally could be shown separately. The entire logic circuit structure is within a single FPGA 106 or other logic device. Alternately, the logic circuit could be placed on multiple logic devices. The same input is received by CORE A and CORE B and their output is monitored by the REDUNDANCY CHECKER for an exact match. The output from the two cores, as well as a failsafe signal from the REDUNDANCY CHECKER are output from the FPGA. An output failsafe gate is used, but not shown in FIG. 1. This feature is described in FIG. 2.

Figure 2:
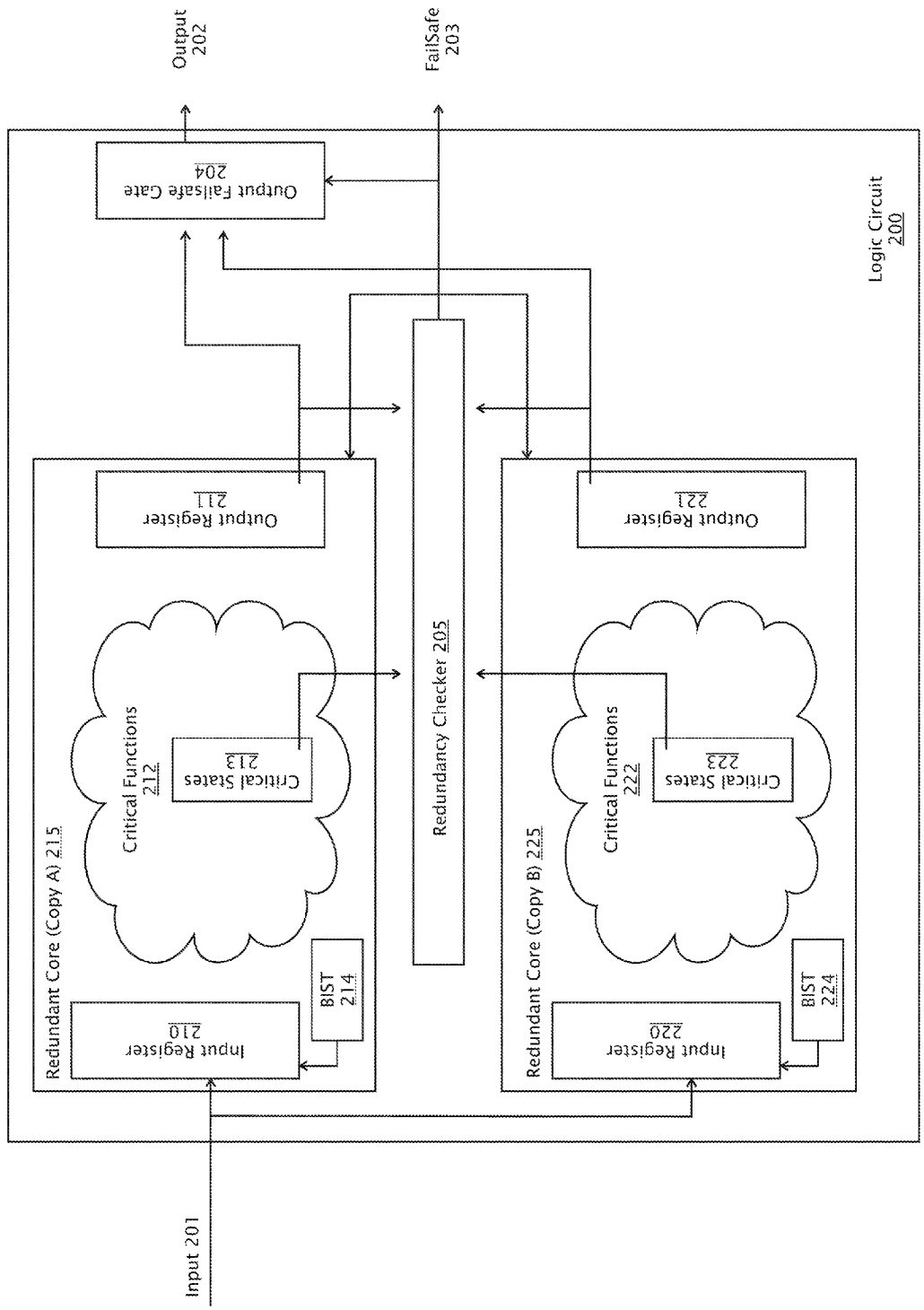
FIGS. 2 and 3 show another graphic illustration of the implementation of two parallel cores utilizing a redundancy checker.

FIG. 2 shows the implementation of two parallel cores utilizing another embodiment of the redundancy checker. Two parallel redundant cores 215, 225 are used to implement the logic circuit. Additional details of the redundant cores are shown which include: input registers 210, 220, output registers 211, 221 and a built in self test (BIST) feature 214, 224. A redundancy checker 205 is used for reliability and error checking and to activate a fail safe mode 203. A portion of the redundant cores is the critical functions, 212, 222 where the critical states 213, 223 variables or information resides. This information is used for error checking by the redundancy checker 205 as shown.

Inputs 201 flow into parallel input registers 210, 220. The input is used by the logic circuit according to the system design and the output registers 211, 221 are updated. The core output then flows from the output register through the output failsafe gate 204 where it is then combined and becomes output 202 for the system. This is a Gate ON communication data output enable. This prevents data from being transmitted when there is a redundancy checker detected failure. An output failsafe 203 is activated by the redundancy checker 205 when an error is detected to alert the system. The failsafe may be a relay contact closure, an alarm, or a communication of some kind. The entire logic circuit 200 resides on a single logic device such as a PAL, CPLD, FPGA, ASIC, or Gate Array. Alternately, the logic circuit could be placed on multiple logic devices.

FIG. 2 is another embodiment of the redundancy checker that is similar to FIG. 1. In FIG. 2, the redundancy checker additionally utilizes critical states (i.e. values) within each redundant core for comparison. This additional information is useful for rapidly uncovering unannounced faults.

The BIST in this case is monitoring the redundant core in the self test.

Figure 3:
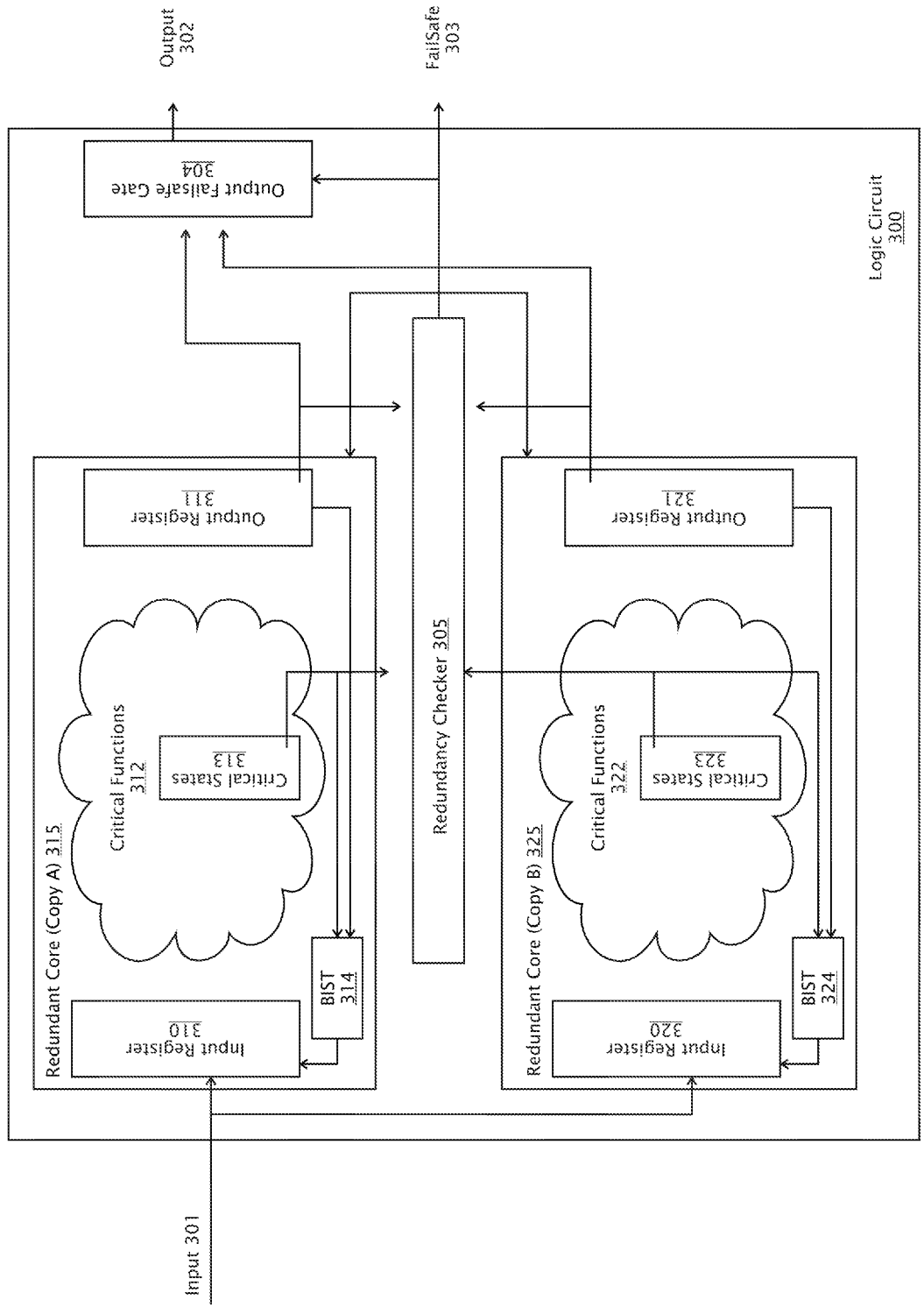

Similarly, FIG. 3 shows another embodiment of the redundancy checker. Two parallel redundant cores 315, 325 are used to implement the logic circuit utilizing: input registers 310, 320, output registers 311, 321 and a built in self test (BIST) feature 314, 324. A redundancy checker 305 is used for reliability and error checking and to activate a fail safe mode 303. A portion of the redundant cores is the critical functions, 312, 322 where the critical states 313, 323 variables or information resides. This information is used for error checking by the redundancy checker 305 as shown.

Similarly, as before, inputs 301 flow into parallel input registers 310, 320. The input is used by the logic circuit according to the system design and the output registers 311, 321 are updated. The core output then flows from the output register through the output failsafe gate 304 where it is then combined and becomes output 302 for the system. An output failsafe 303 is activated by the redundancy checker 305 when an error is detected to alert the system. The entire logic circuit 300 resides on a single logic device. Alternately, the logic circuit could be placed on multiple logic devices.

The BIST in this case additionally uses the critical states and output register in the self test.

Figure 4:
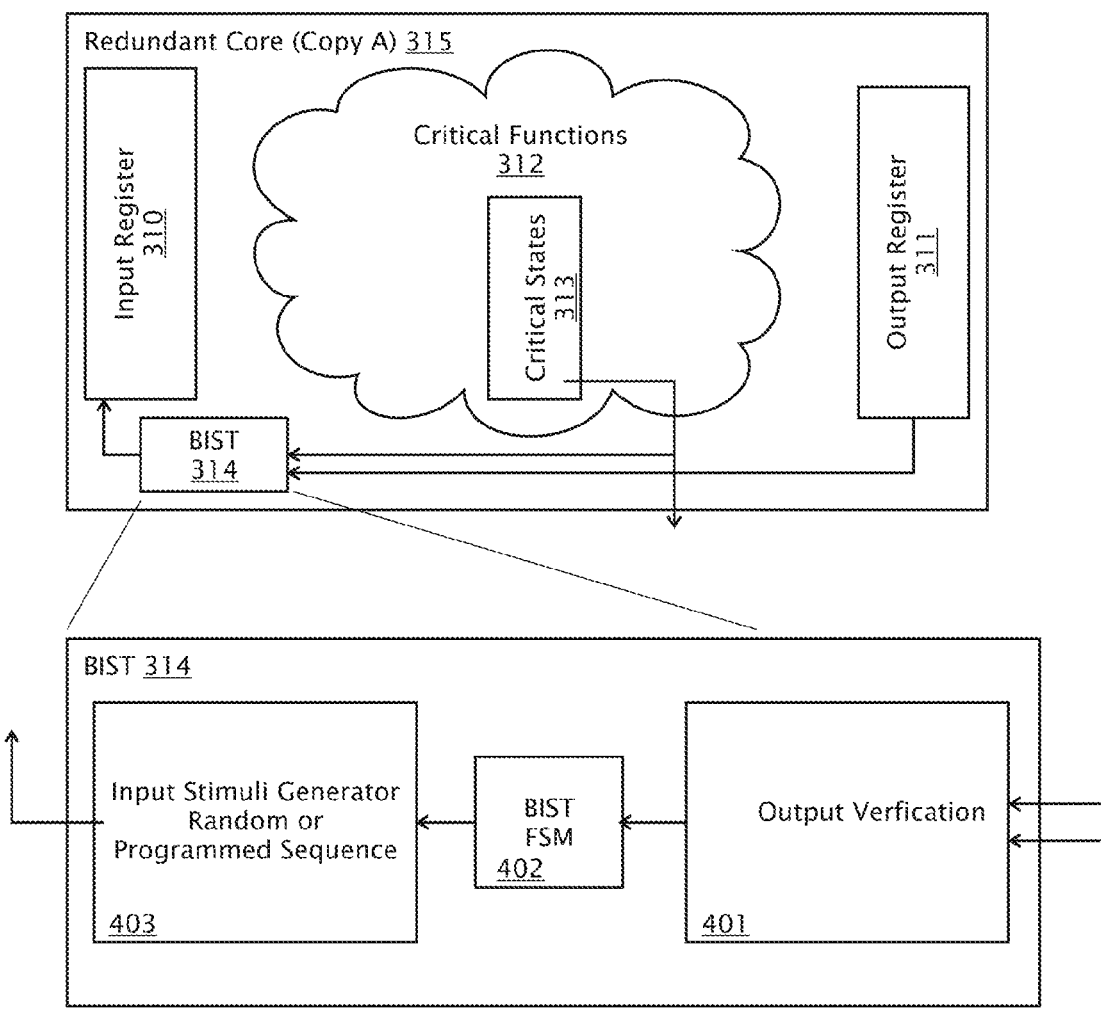
FIG. 4 shows important details of the built in self test of the present invention.

FIG. 4 shows important details of a typical built in self test (BIST) 314. In this case, FIG. 4 is an additional detail from FIG. 3. Output register values from a redundant core 315 and critical states 313 are input to an output verification routine 401 which passes on to a BIST finite state machine (FSM) 402. The BIST is controlled by the FSM. When activated by an operator, timer, or an event, the BIST will generate input stimuli either as a random sequence or as a programmed sequence 403 to the input register 310. The BIST monitors the redundant core, redundant core output, and critical states to verify correct operation. This verification includes: comparing against a stored reference, comparing against another redundant core, or generating a checksum of the monitored output and verifying this against a reference checksum.

It is a preferred embodiment of the present invention to implement the BIST during the normal operation of the logic circuit. That is, to activate the BIST while the logic circuit is performing its mission. This is done without affecting other systems or outputs by methods which include:

1. Freezing outputs during a test.
2. Performing a test during periods of time where outputs are not updated.
3. Placing one of the parallel cores in a specialized test mode, isolating it so that it does not affect the status of any input or output, and disabling the redundancy checkers related to the core being tested.

A typical mission for the logic circuit is to provide a process function between the input and output according to a design. The design may be one of readiness, or a safety related function such as in a plant protection system. The design may be more involved if it is a process control.

The logic circuit mission may also include interfacing with control circuits. They include external logic, decision, detection, and control circuits. These circuits are common in process control and safety related plant decisions. They can be binary (on/off) type of circuits, or they may be control related circuits which includes sensors, switches, process controllers, and actuators. They may be part of a relay based system and interface to other computerized systems.

In another embodiment of the present invention, the redundancy checker is not located on the logic device where the parallel cores are located. The redundancy checker is located separately on another logic device. It is then connected by a communication pathway to the outputs of the cores in order to provide redundancy checking. The redundancy checker then operates as described in FIGS. 1-3, by providing a fail safe signal, etc.

In the preferred embodiment, the present invention is based on a hardware platform rather than a software-based microprocessor system. It is significantly different than a software based microprocessor control system architecture, by implementing the logic circuit in a logic device thereby eliminating executable software and the problems with software based microprocessor systems, such as software common-mode failures. It provides a highly reliable system suitable for safety critical control systems, including reactor protection systems in nuclear plants.

While various embodiments of the present invention have been described, the invention may be modified and adapted to various operational methods to those skilled in the art. Therefore, this invention is not limited to the description and figure shown herein, and includes all such embodiments, changes, and modifications that are encompassed by the scope of the claims.

What is claimed is:

1. A high integrity logic circuit comprising:
   a. a plurality of parallel cores, wherein said parallel cores are used to implement critical functions of said logic circuit,
   b. wherein said parallel cores are redundant or diverse,
   c. a redundancy checker, wherein said redundancy checker is used to:
      i. verify whether a plurality of values from a first parallel core match a plurality of values from a second parallel core, and
      ii. activate said logic circuit into a failsafe state according to a predetermined criterion,
   d. wherein said logic circuit is interfaced to a plurality of inputs and a plurality of outputs,
   e. wherein said logic circuit performs a mission related to said inputs and said outputs, wherein said mission is a safety critical function,
   f. wherein communication between said logic circuit and said inputs and said outputs is protected by at least one item selected from the group consisting of:
      i. redundancy,
      ii. cyclic redundancy check,
      iii. toggle test on said inputs, and
      iv. read back on said outputs,
   g. a built in self test, wherein said built in self test is used to expose unannounced failures in any said parallel core,
   h. wherein said built in self test is performed periodically or continually while said logic circuit performs said mission,
   i. wherein said critical functions of said logic circuit are substantially implemented in at least one logic device, and
   j. wherein said at least one logic device is implemented free of the use of executable software.

2. The high integrity logic circuit according to claim 1 wherein
   a. said redundancy checker is located on a separate logic device from said parallel cores, wherein said redundancy checker is connected to said parallel cores by a communication pathway to outputs of said parallel cores, or
   b. said redundancy checker is located on the same logic device where at least one of said parallel cores reside.

3. A high integrity logic circuit comprising:
   a. a plurality of parallel cores, wherein said parallel cores are used to implement critical functions of said logic circuit, wherein said parallel cores are redundant or diverse, wherein said parallel cores interface with input circuits and output circuits
   b. a redundancy checker, wherein said redundancy checker provides for error detection in said parallel cores comprising:
      i. for discrepancies between said parallel cores, and
      ii. for state changes in critical functions of said logic circuit,
   c. wherein said redundancy checker activates said logic circuit into a failsafe state for any said error detection,
   d. at least one built in self test structure, wherein said built in self test structure exposes failures in critical functions of said logic circuit,
   e. wherein said critical functions of said logic circuit are substantially implemented in at least one logic device, and
   f. wherein said logic device is implemented free of the use of executable software.

4. The high integrity logic circuit according to claim 3 wherein said critical functions of said logic circuit are implemented on a selection from the group consisting of:
   a. a single logic device,
   b. a plurality of logic devices on a single printed circuit board, and
   c. a plurality of printed circuit boards with at least one logic device on each said printed circuit board.

5. The high integrity logic circuit according to claim 3 wherein
   a. said input circuits include at least one item from the group consisting of:
      i. serial bus communication circuits,
      ii. parallel bus communication circuits,
      iii. serial digital channels, and
      iv. parallel digital channels,
   b. said critical functions include at least one item from the group consisting of:
      i. logic decision,
      ii. limit check, and
      iii. state machines,
   c. said output circuits include at least one item from the group consisting of:
      i. serial bus communication circuits,
      ii. parallel bus communication circuits,
      iii. serial digital channels, and
      iv. parallel digital channels.

6. The high integrity logic circuit according to claim 3 wherein
   a. any said input circuit includes at least one item from the group consisting of:
      i. serial communication circuits,
      ii. parallel communication circuits,
      iii. serial digital circuits,
      iv. parallel digital circuits, and
      v. digitized analog circuits,
   b. wherein any said output circuit includes at least one item from the group consisting of:
      i. serial communication circuits,
      ii. parallel communication circuits,
      iii. serial digital circuits,
      iv. parallel digital circuits, and
      v. digitized analog circuits,
   c. wherein any said critical function includes at least one function from the group consisting of:
      i. decision logic,
      ii. detection logic, and
      iii. control logic.

7. The high integrity logic circuit according to claim 3 wherein said redundancy checker receives critical data related to each of said parallel cores, wherein said critical data includes:
   a. critical internal states from said parallel cores, and
   b. critical outputs signals from said parallel cores.

8. The high integrity logic circuit according to claim 3 wherein any said built in self test structure exercises an associated said parallel core for the purpose of exposing unannounced failures.

9. The high integrity logic circuit according to claim 3 wherein said built in self test structure is designed to perform the following:
   a. place a single selected parallel core in a test mode, wherein said test mode does not affect the mission of said logic circuit, or causes undesired actuations of output circuits,
   b. wherein said redundancy checker is disabled for said selected parallel core, c. apply a set of predetermined inputs to at least one input or internal states of said selected parallel core, d. verify the response of said selected parallel core to said set of predetermined inputs through internal state changes and selected parallel core outputs, and e. restore said selected parallel core and restore redundancy checker to normal operation.

10. The high integrity logic circuit according to claim 3 wherein said built in self test structure is designed to perform the following:

a. place said logic circuit in test mode, wherein said test mode ensures no undesired actuations of output circuits, b. apply a set of identical predetermined inputs to all of said parallel cores, and c. verify the response of all of said parallel cores to said set of identical predetermined inputs by use of said redundancy checker.

11. The high integrity logic circuit according to claim 3 wherein a. said logic circuit is implemented using at least three parallel cores, b. at least two parallel cores are interfaced to a plurality of inputs and a plurality of outputs in an operational mode, c. wherein said logic circuit operates said outputs based on said inputs according to a predetermined criterion, and d. a single selected parallel core is periodically removed from operational mode and placed in test mode, wherein said test mode comprises:

i. isolating said selected parallel core from affecting the status of any said inputs or said outputs, ii. applying a set of predetermined inputs to at least one input or internal states of said selected parallel core, iii. verifying the correct response of said selected parallel core to said set of predetermined inputs through internal state changes and selected parallel core outputs, and iv. restoring said selected parallel core to normal operation.

12. The high integrity logic circuit according to claim 3 wherein all said parallel cores and all said redundancy checkers are implemented within said logic circuit.

13. The high integrity logic circuit according to claim 3 wherein said at least one logic device comprises a PAL, CPLD, FPGA, ASIC, or Gate Array.

14. The high integrity logic circuit according to claim 3 wherein said redundancy checker is located on a separate logic device from said parallel cores or said redundancy checker is located on the same logic device where at least one of said parallel cores reside.

15. A high integrity logic circuit comprising:

a. a plurality of parallel cores, wherein said parallel cores are used to implement critical functions of said logic circuit, b. wherein at least one of said parallel cores is implemented in a logic device, wherein said logic device is free of the use of executable software, c. wherein at least one of said parallel cores is implemented using executable software in a processor, d. a redundancy checker, wherein said redundancy checker is used to:

i. verify whether a plurality of values from a first parallel core match a plurality of values from a second parallel core, and ii. activate said logic circuit into a failsafe state according to a predetermined criterion, e. wherein said logic circuit is interfaced to a plurality of inputs and a plurality of outputs, f. wherein said logic circuit performs a mission related to said inputs and said outputs, g. wherein communication between said logic circuit and said inputs and said outputs is protected by at least one item selected from the group consisting of:

i. redundancy, ii. cyclic redundancy check, iii. toggle test on said inputs, and iv. read back on said outputs, h. a built in self test, wherein said built in self test is used to expose unannounced failures in any said parallel core, and i. wherein said built in self test is performed periodically or continually while said logic circuit performs said mission.

16. A method of failure detection in a logic circuit and mitigating the failure's effect comprising:

a. providing a plurality of parallel cores, wherein said parallel cores are used to implement critical functions of said logic circuit, wherein said parallel cores are redundant or diverse, b. providing a redundancy checker, wherein said redundancy checker provides error detection in said parallel cores comprising:

i. for discrepancies between said parallel cores, and ii. for state changes in critical functions of said logic circuit, c. wherein said redundancy checker is used to activate said logic circuit into a failsafe state for any said error detection, d. providing at least one built in self test structure, wherein said built in self test structure is used to expose failures in critical functions of said logic circuit, e. providing at least one logic device, wherein said critical functions of said logic circuit are substantially implemented within said at least one logic device, and f. wherein any said logic device is implemented free of the use of executable software, whereby said logic circuit is monitored for said failure detection by said error detection and said built in self test, and whereby said failure's effect is mitigated by said failsafe state.

17. The method according to claim 16 wherein said critical functions of said logic circuit are implemented on a selection from the group consisting of:

a. a single logic device, b. a plurality of logic devices on a single printed circuit board, and c. a plurality of printed circuit boards with at least one logic device on each said printed circuit board.

18. The method according to claim 16 wherein said parallel cores interface with input circuits and output circuits.

19. The method according to claim 18 wherein a. said input circuits include at least one item from the group consisting of:

i. serial bus communication circuits, ii. parallel bus communication circuits, iii. serial digital channels, and iv. parallel digital channels, b. said critical functions include at least one item from the group consisting of:

i. logic decision, ii. limit check, and iii. state machines, c. said output circuits include at least one item from the group consisting of:
  i. serial bus communication circuits,
  ii. parallel bus communication circuits,
  iii. serial digital channels, and
  iv. parallel digital channels.

20. The method according to claim 18 wherein
  a. any said input circuit includes at least one item from the group consisting of:
    i. serial communication circuits,
    ii. parallel communication circuits,
    iii. serial digital input circuits,
    iv. parallel digital input circuits, and
    v. digitized analog input circuits,
  b. wherein any said output circuit includes at least one item from the group consisting of:
    i. serial communication circuits,
    ii. parallel communication circuits,
    iii. serial digital Input circuits,
    iv. parallel digital Input circuits, and
    v. digitized analog Input circuits,
  c. wherein any said critical function includes at least one function from the group consisting of:
    i. decision logic,
    ii. detection logic, and
    iii. control logic.

21. The method according to claim 16 wherein said redundancy checker receives critical data related to each of said parallel cores, wherein said critical data includes:
  a. critical internal states from said parallel cores, and
  b. critical outputs signals from said parallel cores.

22. The method according to claim 16 wherein any said built in self test structure exercises an associated said parallel core for the purpose of exposing unannounced failures.

23. The method according to claim 16 wherein said built in self test structure is designed to perform the following items:
  a. place a single selected parallel core in a test mode, wherein said test mode does not affect the mission of said logic circuit, or causes undesired actuations of output circuits,
  b. wherein said redundancy checker is disabled for said selected parallel core,
  c. apply a set of predetermined inputs to at least one input or internal states of said selected parallel core,
  d. verify the response of said selected parallel core to said set of predetermined inputs through internal state changes and selected parallel core outputs, and
  e. restore said selected parallel core and restore redundancy checker to normal operation.

24. The method according to claim 16 wherein said built in self test structure is designed to perform the following items:
  a. place said logic circuit in test mode, wherein said test mode ensures no undesired actuations of output circuits,
  b. apply a set of identical predetermined inputs to all of said parallel cores, and
  c. verify the response of all of said parallel cores to said set of identical predetermined inputs by use of said redundancy checker.

25. The method according to claim 16 wherein said logic circuit is implemented using at least three parallel cores, wherein
  a. at least two parallel cores are interfaced to a plurality of inputs and a plurality of outputs in an operational mode,
  b. wherein said logic circuit operates said outputs based on said inputs according to a predetermined criterion, and
  c. a single selected parallel core is periodically removed from operational mode and placed in test mode, wherein said test mode comprises:
    i. isolating said selected parallel core from affecting the status of any said inputs or said outputs,
    ii. applying a set of predetermined inputs to at least one input or internal states of said selected parallel core,
    iii. verifying the correct response of said selected parallel core to said set of predetermined inputs through internal state changes and selected parallel core outputs, and
    iv. restoring said selected parallel core to normal operation.

26. The method according to claim 16 wherein all said parallel cores and all said redundancy checkers are implemented within said logic circuit.

27. The method according to claim 16 wherein said at least one logic device comprises a PAL, CPLD, FPGA, ASIC, or Gate Array.

28. The high integrity logic circuit according to claim 16 wherein said redundancy checker is located on a separate logic device from said parallel cores or said redundancy checker is located on the same logic device where at least one of said parallel cores reside.

29. A method of failure detection in a logic circuit and mitigating the failure's effect comprising:
  a. providing a plurality of parallel cores, wherein said parallel cores are used to implement critical functions of said logic circuit,
  b. wherein at least one of said parallel cores is implemented in a logic device, wherein said logic device is free of the use of executable software,
  c. wherein at least one of said parallel cores is implemented using executable software in a processor,
  d. providing a redundancy checker, wherein said redundancy checker is used to:
    i. verify whether a plurality of values from a first parallel core match a plurality of values from a second parallel core, and
    ii. activate said logic circuit into a failsafe state according to a predetermined criterion,
  e. providing a plurality of inputs and a plurality of outputs, wherein said logic circuit is interfaced to said plurality of inputs and to said plurality of outputs,
  f. wherein said logic circuit performs a mission related to said inputs and said outputs,
  g. wherein communication between said logic circuit and said inputs and said outputs is protected by at least one item selected from the group consisting of:
    i. redundancy,
    ii. cyclic redundancy check,
    iii. toggle test on said inputs, and
    iv. read back on said outputs,
  h. providing a built in self test, wherein said built in self test is used to expose unannounced failures in any said parallel core, and
  i. wherein said built in self test is performed periodically or continually while said logic circuit performs said mission,
  whereby said logic circuit is monitored for said failure detection by said redundancy checker and said built in self test, and
  whereby said failure's effect is mitigated by said failsafe state.

30. A method of failure detection in a logic circuit and mitigating the failure's effect comprising:
- a. providing a plurality of parallel cores, wherein said parallel cores are used to implement critical functions of said logic circuit,
- b. wherein said parallel cores are redundant or diverse,
- c. providing a redundancy checker, wherein said redundancy checker is used to:
  - i. verify whether a plurality of values from a first parallel core match a plurality of values from a second parallel core, and
  - ii. activate said logic circuit into a failsafe state according to a predetermined criterion,
- d. providing a plurality of inputs and a plurality of outputs, wherein said logic circuit is interfaced to said plurality of inputs and said plurality of outputs,
- e. wherein said logic circuit performs a mission related to said inputs and said outputs,
- f. wherein communication between said logic circuit and said inputs and said outputs is protected by at least one item selected from the group consisting of:
  - i. redundancy,
  - ii. cyclic redundancy check,
  - iii. toggle test on said inputs, and
  - iv. read back on said outputs,
- g. providing a built in self test, wherein said built in self test is used to expose unannounced failures in any said parallel core,
- h. wherein said built in self test is performed periodically or continually while said logic circuit performs said mission,
- i. wherein said critical functions of said logic circuit are substantially implemented in at least one logic device, and
- j. wherein said at least one logic device is implemented free of the use of executable software, whereby said logic circuit is monitored for said failure detection by said error detection and said built in self test, and whereby said failure's effect is mitigated by said failsafe state.

* * * * *